United States Patent [19]

Chang et al.

[11] Patent Number: 5,093,270

[45] Date of Patent: Mar. 3, 1992

[54] METHOD FOR ENHANCING SIGNAL RELEASE FROM LIPOSOMES USING WATER-MISCIBLE ALCOHOLS

[75] Inventors: Steve C. S. Chang, Franklin, Mass.; Say-Jong Law, Westwood, Mass.

[73] Assignee: Ciba Corning Diagnostics Corp., Medfield, Mass.

[21] Appl. No.: 356,083

[22] Filed: May 24, 1989

[51] Int. Cl.$^5$ .................. G01N 33/546; G01N 33/543
[52] U.S. Cl. ..................... 436/518; 436/829; 424/450; 252/700; 435/968
[58] Field of Search ............. 436/518, 829; 264/4.3, 264/4.1; 252/700; 435/28, 968

[56] References Cited

U.S. PATENT DOCUMENTS 4,708,933 11/1987 Huang et al. .................. 435/7
4,814,270 3/1989 Piran ............................ 435/7
4,927,769 5/1990 Chang et al. .................. 436/518

OTHER PUBLICATIONS

Ellefson et al., "Chapter 10–Lipids and Lipoproteins", *Fundamentals of Clinical Chemistry*, pp. 474, 489–491, 507–511, 1976.

*Primary Examiner*—Esther L. Kepplinger
*Assistant Examiner*—Carol E. Bidwell
*Attorney, Agent, or Firm*—Arthur S. Morgenstern; Nicholas I. Slepchuk, Jr.

[57] ABSTRACT

A method for releasing encapsulated marker molecules from within liposomes comprises contracting the liposomes with an effective amount of a water-miscible alcohol. The chemiluminescence of acridinium esters is enhanced by oxidizing the acridinium ester in the presence of an effective amount of a water-miscible alcohol.

8 Claims, No Drawings

METHOD FOR ENHANCING SIGNAL RELEASE FROM LIPOSOMES USING WATER-MISCIBLE ALCOHOLS

FIELD OF THE INVENTION

This invention relates to a method for releasing encapsulated marker molecules from within liposomes using water-miscible alcohols. In particular, this invention relates to a method for releasing encapsulated chemiluminescent marker molecules from within liposomes using water-miscible alcohols.

This invention also relates to a method for the enhancement of the chemiluminescence of acridinium esters using water-miscible alcohols.

BACKGROUND OF THE INVENTION

In the clinical treatment and diagnosis of disease, assay systems which detect and quantitatively measure biologically important molecules are frequently employed, e.g., immunoassays and DNA/RNA detection assays. Liposomes provide certain advantages when used in these assay systems. For example, the use of liposomes can increase assay sensitivity because of the large number of marker molecules which can be encapsulated within a liposome vesicle.

Several types of marker molecules have been encapsulated in liposome vesicles including enzymatic, colorimetric, chromogenic, fluoregenic, radiometric, bioluminescent and chemiluminescent marker molecules. Chemiluminescent marker molecules, such as acridinium esters, have increasingly become the marker molecules of choice in clinical assay systems because they impart high sensitivity and wide linear range to most assays.

The marker molecules encapsulated within the liposome vesicle are most often released from the liposomes by complement-mediated vesicle lysis. See, e.g., U.S. Pat. No. 4,342,826. Other known methods for releasing the marker molecules from the liposomes include the use of lipolytic enzymes to lyse the vesicles. However, these known procedures are frequently inadequate for certain types of assays. For example, the use of liposomes with encapsulated chemiluminescent markers in a solid phase immunoassay requires a quicker and more complete release of the marker molecule than is provided by the above-identified methods.

U.S. Pat. No. 4,372,745 describes the use of liposomes with encapsulated fluorescent compounds in an immunoassay. This assay describes the use of a detergent (TRITON X-100) to break the liposome vesicles and release the fluorescent compounds. (TRITON is a registered trademark of the Rohm and Haas Company. TRITON X-100 is a non-ionic detergent of the polyethylene glycol p-isooctylphenyl there type having the formula

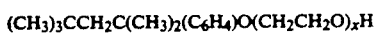

where x averages 10.) See also U.S. Pat. Nos. 4,372,745 and 4,707,453 (use of TRITON X-100 to rupture liposomes), and U.S. Pat. No. 4,704,355 (use of saponin detergent to rupture liposomes). This procedure is not effective for use with certain marker molecules, such as chemiluminescent compounds, because the detergent (and certain other organic lytic agents like dimethyl sulfoxide) generate a high background signal (noise).

U.S. Pat. No. 4,927,769 (Application Ser. No. 071,660, filed on July 8, 1987), describes a method for enhancing the chemiluminescent signal of an acridinium ester which comprises oxidizing the acridinium ester in the presence of an effective amount of an enhancer selected from the group consisting of a cationic surfactant, a nonionic surfactant, and a sulfated primary alcohol.

Accordingly, it is an object of this invention to provide a novel method for releasing a marker molecule from within a liposome vesicle, which is quicker, more complete and generates less background interference than known methods for such release.

It is an another object of the present invention to provide a novel method for enhancing the chemiluminescence of acridinium esters using water-miscible alcohols.

DESCRIPTION OF THE INVENTION

This invention relates to a method for releasing a marker molecule from within a liposome vesicle encapsulating the marker molecule which comprises contacting the liposome vesicle with an effective amount of a water-miscible alcohol.

Liposomes useful in the method of this invention can be prepared by any of the various known methods to produce either unilamellar vesicles or multilamillar vesicles. The liposomes are single or multicompartmented bodies obtained when lipids or lipid mixtures are dispersed in an aqueous suspension containing the marker molecules.

As an example of one method for producing liposomes, lipids are physically dispersed into an aqueous solution, and a dry film of lipids is formed on the interior surface of a suitable vessel. The aqueous solution containing the marker compounds to be entrapped within the liposomes is then placed in the vessel in contact with the lipid film. The lipid film is then dispersed in the aqueous solution by vigorous agitation or sonification.

Numerous other methods exist for forming the liposomes useful for use in the method of this invention and it is left to the artisan to choose the method best suited for his desired use. A preferred method for manufacturing liposomes is disclosed in U.S. Pat. No. 4,933,121 (copending U.S. application Ser. No. 940,519, field on Dec. 10, 1986), herein incorporated by reference.

The marker molecule or marker compound useful in the method of this invention can be any marker molecule capable of being encapsulated within a liposome vesicle. A marker molecule for the purpose of this invention is any molecule which is directly or indirectly involved with the production of a detectable signal. Suitable marker compounds include fluorogenic agents such as fluorescent dyes, colorigenic agents such as phosphodinitrophenol, and, preferably, chemiluminescent agents such as luminol and acridinium esters, and conjugates thereof. A preferred group of acridinium esters are hydrophilic polysubstituted arylacridinium esters. These esters are highly soluble in water and can be encapsulated in liposomes at high concentrations.

Preferred acridinium esters include acridinium esters of the following formula:

$$-O-, -S-, -NH-, -\underset{\underset{O}{\|}}{C}-, \text{diazo}, -\underset{\underset{O}{\|}}{NHCNH}-,$$

$$-\underset{\underset{S}{\|}}{NHCNH}-, -\underset{\underset{O}{\|}}{NHC}-, -\underset{\underset{O}{\|}}{NHCO}-,$$

$$-\underset{\underset{O}{\|}}{CNH}-, \text{ or } -\underset{\underset{+NH_2}{\|}}{NHC}-;$$

and R is alkyl, alkenyl, alkynyl, aryl, or aralkyl, of from 1 to 24 carbon atoms, containing from 0 to 20 heteratoms selected from the group consisting of nitrogen, oxygen, phosphorous, and sulfur.

An ionizable group for the purposes of this invention is any functional group which retains a net positive or negative charge within a specific pH range. Preferably the functional group will retain a net positive or negative charge within the range of pH2-10 and, more preferably, within the range of pH5-9. I can be any ionizable group provided that the ionizable group is not deleterious to the encapsulation of the acridinium ester of this invention within the liposome. I is preferably $-SO_3H$, $-OSO_3H$, $-PO(OH)_2$, $-OPO_3$, or $-COOH$ and n is preferably about 1 to about 20 and, more preferably, less than about 10.

More preferably, $R_1$ is alkyl of from 1 to 10 carbon atoms; $R_2$, $R_3$, $R_5$, and $R_7$ are hydrogen, nitro, $-CN$, halide, alkoxyl of from 1 to 4 carbon atoms, amino, or $-SO_3$; and $R_4$ and $R_8$ are alkyl of from 1 to 4 carbon atoms.

Most preferably, $R_1$, $R_4$, and $R_8$ are methyl; $R_2$, $R_3$, $R_5$, and $R_7$ are hydrogen; X is bromide; $R_6$ is $-Q-R-I_{(n)}$, Q is a $$-\underset{\underset{O}{\|}}{C}- \text{ and } -R-I_{(n)}$$

is selected from the group consisting of aminomethane sulfonic acid, 7-amino-1,3-naphthalenedisulfonic acid, S-(3-sulfopropyl)cysteine, 2-aminoethyl hydrogen sulfate, 2-aminoethylphosphonic acid, and 2-aminoethyl dihydrogen phosphate.

The $R_5$ and $R_6$ position can be interchanged in the acridinium esters of this invention. Accordingly, the preferred acridinium esters of this invention include acridinium esters of the following formula:

wherein $R_1$, $R_2$, $R_3$, $R_4$, $R_5$, $R_6$, $R_7$, $R_8$, and X are as defined above. It is to be understood that any marker molecule whose production of a detectable signal is deleteriously affected by the alcohol is not intended for

--- wherein $R_1$ is alkyl, alkenyl, alkynyl, aryl, or aralkyl, containing from 0 to 20 heteroatoms, preferably nitrogen, oxygen, phosphorous or sulfur;

$R_2$, $R_3$, $R_5$, and $R_7$ are hydrogen, amino, alkoxyl, hyroxyl, -COOH, halide, nitro, $$-CN, -SO_3H, -\underset{\underset{O}{\|}}{NHCR}, -\underset{\underset{O}{\|}}{CR},$$

$$-\underset{\underset{O}{\|}}{COR}, -\underset{\underset{O}{\|}}{CNHR}, \text{ or } -SCN,$$

wherein R is alkyl, alkenyl, alkynyl, aryl, or aralkyl, containing from 0-20 heteratoms;

$R_4$ and $R_8$ are hydrogen, alkyl, alkenyl, alkynyl, aralkyl, or alkoxyl;

X is an anion, preferably $CH_3SO_4^-$, $OSO_2F^-$, halide, $OSO_2CF_3^-$, $OSO_2C_4F_9^-$, or $$-OSO_2-\underset{}{\bigcirc}-CH_3;$$

and $R_6$ is:

$$-R-I_{(n)} \text{ or } -Q-R-I_{(n)}$$

wherein R is as defined above; Q is $$-O-, -S-, -NH-, -\underset{\underset{O}{\|}}{C}-, -SO_3-,$$

$$\text{diazo}, -\underset{\underset{S}{\|}}{NHCNH}-, -\underset{\underset{O}{\|}}{NHCNH}-, -\underset{\underset{O}{\|}}{NHCO}-,$$

$$-\underset{\underset{O}{\|}}{NHC}-, -\underset{\underset{O}{\|}}{CNH}-, \text{ or } -\underset{\underset{+NH_2}{\|}}{NHC}-;$$

I is an ionizable group; and n is at least 1.

Preferably $R_1$ is alkyl, alkenyl, alkynyl, aryl or aralkyl of from 1 to 24 carbon atoms;

$R_2$, $R_3$, $R_5$ and $R_7$ are hydrogen, amino, $-CO_2$, cyano, hydroxyl, alkoxyl of from 1 to 4 carbon atoms, nitro, halide, $-SO_3$, or $-SCN$;

$R_4$ and $R_8$ are preferably hydrogen or alkyl, alkenyl, alkynyl, or alkoxyl, of from 1 to 8 carbon atoms; X is halide;

$R_6$ is $-Q-R-I_{(n)}$; Q is use in the method of this invention. For example, certain enzymes, such as glucose-6-phosphate dehydrogenase, are not suitable for use in the method of this invention because the alcohol will destroy the enzymatic activity of these enzymes.

The alcohols useful in the method of this invention are water-miscible alkyl compounds containing one or more hydroxyl groups. The expression "water-miscible", for the purposes of this invention, means the absence of a precipitate or separation of two layers when the alcohol is immersed in an aqueous solution at any proportion. Preferred alcohols are alcohols containing one to three carbon atoms and one hydroxyl group. Particularly preferred is isopropanol.

The alcohol useful in the method of this invention must be present in an amount which is effective to rupture the liposome vesicle. This amount can vary depending on the alcohol utilized and should be determined empirically. Preferably, the liposome is contacted with an aqueous solution comprising about 10% to 90% (volume to volume) alcohol, more preferably about 25% to 90% (volume to volume) alcohol, and most preferably about 50% to 90% (volume by volume) alcohol. The aqueous solution can comprise other reagents and/or components (e.g. HCl) provided that these reagents and components do not deleteriously affect the utility of the marker molecule.

The conditions under which the liposome vesicles are contacted with the alcohol will depend primarily on the choice of liposome, marker molecule, and water-miscible alcohol. However, secondary reaction conditions such as temperature, pH, and incubation time will also effect the amount of rupture of the liposomes. The secondary reaction conditions should be adjusted to obtain maximum rupturing of the liposomes while producing minimal background noise. Preferably, the liposomes are contacted with the alcohol between about 4° C. and about 37° C.; between about pH 1 and about pH 10; and for about 1 sec. to about 60 sec.

The method of this invention is useful in procedures in which liposomes are used as tracer compounds. The method of this invention is particularly useful in solid phase immunoassays in which liposomes encapsulating acridinium esters are used as a chemiluminescent label.

This invention also relates to a method for enhancing the chemiluminescent signal of an acridinium ester in a chemiluminescent reaction which comprises oxidizing the acridinium ester in the presence of an effective amount of a water-miscible alcohol.

The acridinium esters whose signal can be enhanced by the method of this invention can be any acridinium ester which can generate a chemiluminescent signal in a chemiluminescent reaction. Examples of useful acridinium esters are disclosed in U.S. Pat. No. 4,745,181, the pertinent disclosure of which is incorporated by reference herein.

The water-miscible alcohols useful for enhancing the chemiluminescent signal of an acridinium ester according to the method of this invention are described above.

The acridinium ester can be oxidized by any oxidant which reacts with the acridinium ester under alkaline pH conditions to cause conversion of the ester to a light-emitting species in a chemiluminescent reaction. A preferred oxidant is hydrogen peroxide in dilute alkali.

For the purposes of this invention, "enhancing" means that the total light emission of the chemiluminescent reaction and/or the signal to background noise ratio of the chemiluminescent reaction is greater than that achieved by the acridinium ester in the absence of the water-miscible alcohol.

The effective amount of water-miscible alcohol necessary to enhance the chemiluminescent signal of the acridinium ester in a chemiluminescent reaction will vary depending on the alcohol selected and should be determined empirically. As a general rule, an effective amount of water-miscible alcohol in a chemiluminescent reaction mixture is greater than about 10% volume to volume, preferably greater than 50% volume to volume. Light emission from the chemiluminescent reaction of this invention will depend primarily on the choice of acridinium ester, oxidant, and water-miscible alcohol. However, secondary reaction conditions such as temperature, pH, reagent concentration, mixing speed and method of light measurement will also effect the amount of light emitted. The secondary reaction conditions should be adjusted to obtain maximum light emission with the signal to background noise ratio as high as possible. Preferably, the chemiluminescent reaction should be conducted between about 20° C. and about 25° C.; above about pH 10; and for about 2 sec. to about 4 sec.

The method of this invention is useful in procedures in which acridinium esters are used as chemiluminescent tracers and is particularly useful in immunoassays and assays involving nucleic acids, e.g., DNA or RNA probes, in which an acridinium ester is used as a chemiluminescent label.

The skilled artisan will appreciate that in situations wherein liposomes encapsulating acridinium esters are used as tracer compounds, use of the water-miscible alcohols of this invention will both facilitate rupturing the liposome vesicles to release the acridinium ester and enhance the signal generated by the released acridinium esters in a chemiluminescent reaction.

The following examples are presented to illustrate the present invention.

EXAMPLE 1

Release of Liposome-Encapsulated IqG-Acridinium Ester Using Ethanol

A. Preparation of IgG—acridinium ester (IgG-AE) conjugate:

250 ug of mouse IgG in Buffer (0.1M sodium phosphate and 0.15M sodium chloride, pH 8.0) was reacted with 200 ul of 4-(2-succinimidyloxycarbonylethyl)phenyl-10-methylacridinium-9-carboxylate methosulphate (0.2 mg/ml in dimethylformamide) for 15 minutes at room temperature to form a reaction mixture.

500 ul of lysine (10 mg/ml in Buffer) was added to the reaction mixture to stop the reaction. The stopped reaction mixture was passed through a 1×10 cm Sephadex G-25 column and eluted with Buffer. The IgG-AE conjugate emerged from the column with the void volume. Uncoupled acridinium ester was retained by the column. The eluted IgG-AE conjugate was diluted ten fold with phosphate buffered saline (10mM phosphate, pH 7.4) containing 1 mg/ml bovine serum albumin.

B. Preparation of the IgG-AE conjugate encapsulated T$_4$-liposomes:

11 ml of the IgG-AE conjugate prepared in A (1 mg/ml) was dialyzed against 1 liter of deionized water for at least 5 hours with 1 change of deionized water. The dialyzed conjugate was lyophilized. The lyophilized residue was dissolved in 1.2 ml of Glycerol Buffer (2.7% glycerol/0.5mM EDTA, pH 6.0). The resulting solution was filtered through a 0.4 um polycarbonate membrane (13 mm, Nucleopore Corp.,Pleasanton, CA) to produce a filtrate.

A lipid mixture film was prepared by combining N-[3-(α-carboxy-3',3',5,5'-tetraiodo-L-thyronyl)propionyl](1,2-dipalmitoyl-3-rac-phosphatidyl)ethanolamine (PE-Suc-T$_4$) (0.2 mg, OD 300=4.0/ul of chloroform), prepared as described in copending U.S. application Ser. No. 094,667, filed Sept. 9, 1987, the pertinent disclosure of which is incorporated by reference herein, with 25 mg of dipalmitoyl phosphatidylcholine, 13.5 mg cholesterol, and 2.3 mg of dipalmitoyl phosphatidylglycerol, in 1.0 ml of chloroform in a 100 ml round bottom flask and evaporating the resultant solution to dryness at 30° C. on a rotary evaporater in vacuo.

The filtrate containing the IgG-AE conjugate was added to the round bottom flask containing the dried lipid mixture film and the flask was heated at 42° C. for 3 minutes on a rotary evaporater, to produce liposomes. The liposomes so produced were extruded sequentially without delay through 1.0, 0.6, and 0.4 um polycarbonate membranes (13mm, Nucleopore Corp.). The extruded liposomes were washed by centrifugation in 7 ml of Glycerol Buffer four times for 75 minutes each. The resulting liposome pellet was resuspended in 2 ml of Glycerol Buffer.

C. Comparison of different preparations of IgG-AE liposomes:

10 ul aliquots of four separate liposome preparations prepared as described in B were pipetted into 12×50mm tubes. To the control samples was added 100 ul of 0.1 N HCl without any alcohol. To the test samples was added 100 ul of 90% ethanol in 0.1N HCl. Immediately after addition of the respective HCl or HCl/ethanol solutions, 300 ul of 0.1N NaOH containing 0.1% H$_2$O$_2$ was added to each control tube and test tube, and signal from each tube was measured in a LB950 Luminometer (available from Laboratorium Prof. Dr. Berthold, Wildbad, West Germany) in Counts Per Second (CPS). The results are listed below in Table 1.

TABLE 1

| Liposome Preparation | Control CPS* (0.1N HCl Only) | Test CPS* (0.1N HCl + Ethanol) |
|---|---|---|
| 1 | 6960 | 121,170 |
| 2 | 6520 | 100,490 |
| 3 | 5160 | 49,930 |

TABLE 1-continued

| Liposome Preparation | Control CPS* (0.1N HCl Only) | Test CPS* (0.1N HCl + Ethanol) |
|---|---|---|
| 4 | 3760 | 85,020 |

*The difference in background counts between the control solution (0.1N HCl without liposomes) and the test solution (90% ethanol in 0.1N HCl without liposome) was less than 300 counts.

D. Effect of ethanol concentration on the signal release:

10 ul aliquots of a single preparation of liposomes prepared as described in B were pipetted into 12×50mm tubes. To each tube was added 100 ul of a solution of 0.1N HCl plus varying amounts of ethanol (see Table 2). Immediately after addition of the respective HCl solutions, 300 ul of 0.1N NaOH containing 0.1% H$_2$O$_2$ was added to each tube and the signal from each tube was measured in a LB950 Luminometer in CPS. The results are listed in Table 2.

TABLE 2

| Tube | % Ethanol in 0.1N HCl | CPS |
|---|---|---|
| 1 | 0 | 6540 |
| 2 | 10 | 7450 |
| 3 | 25 | 9680 |
| 4 | 50 | 33780 |
| 5 | 90 | 64080 |

EXAMPLE 2

Comparison of Several Different Alcohols as Signal-Releasing Agents 10 ul aliquots of a single liposome preparation prepared as described in Example 1B were pipetted into 12×50mm tubes. To each of duplicate sets of tubes was added 100 ul of a solution of 0.1N HCl minus alcohol or 0.1N HCl plus varying amounts of certain alcohols as described in Table 3. One set of tubes contained only 0.1N HCl (no alcohol and no liposomes) and was used to measure background. Immediately after addition of the respective HCl solutions, 300 ul of 0.1N NaOH containing 0.1% H$_2$O$_2$ was added to each tube and the signal from each tube was read in a LB950 Luminometer. The signal generated from each tube containing liposomes (SIGNAL) was divided by the signal generated by the corresponding tube without liposomes (NOISE) to calculate a Signal to Noise (S/N) Ratio. The results are listed in Table 3.

TABLE 3

| Tube | Alcohol | % Alcohol in 0.1N HCl | Signal | Noise | S/N Ratio | Relative S/N Ratio Over Control |
|---|---|---|---|---|---|---|
| 1 | Ethanol | 90 | 63096 | 2314 | 27.3 | 5.5 |
| 2 | Ethylene glycol | 90 | 16400 | 1440 | 11.4 | 2.3 |
| 3 | Ethylene glycol | 50 | 12970 | 2430 | 5.3 | 1.1 |
| 4 | Ethylene glycol | 25 | 11440 | 1810 | 6.3 | 1.3 |
| 5 | Ethylene glycol | 12.5 | 9960 | 1600 | 6.2 | 1.2 |
| 6 | 1-Propanol | 90 | 151680 | 2260 | 67.1 | 13.4 |
| 7 | 1-Propanol | 50 | 79340 | 1580 | 50.2 | 10.0 |
| 8 | 1-Propanol | 25 | 43220 | 1490 | 29.0 | 5.8 |
| 9 | 2-Propanol | 90 | 154350 | 2120 | 72.8 | 14.6 |
| 10 | 2-Propanol | 50 | 81010 | 1900 | 42.6 | 8.5 |
| 11 | 2-Propanol | 25 | 24730 | 1770 | 13.9 | 2.8 |
| 12 | 1,2-Propandiol | 90 | 54870 | 2430 | 22.5 | 4.5 |

TABLE 3-continued

| Tube | Alcohol | % Alcohol in 0.1N HCl | Signal | Noise | S/N Ratio | Relative S/N Ratio Over Control |
|---|---|---|---|---|---|---|
| 13 | 1,2-Propandiol | 50 | 35740 | 1890 | 18.9 | 3.8 |
| 14 | 1,2-Propandiol | 25 | 22950 | 1450 | 15.8 | 3.2 |
| 15 | Control (0.1N Hcl) | 0 | 11220 | 2210 | 5.0 | 1.0 |

EXAMPLE 3

Direct Enhancement of Signal by Alcohols

The following experimental results demonstrate that a direct enhancement of signal generated by acridinium ester could be achieved by the same alcohols with significant (but less) magnitude. The $T_3$-BGG-AE conjugate was used as an example, and conjugation of the acridinium ester to $T_3$-BGG (a derivative of bovine gamma globulin) was done by the same method as described in Example 1A.

The $T_3$-BGG-AE conjugate prepared was diluted in PBS/BSA (10mM phosphate, 0.15M sodium chloride, 1mg/ml bovine serum albumin, pH 7.4) so that 50 ul of the diluted $T_3$-BGG-AE conjugate produces 360,000 CPS.

Into 12×50mm tubes was pipetted either 50 ul of PBS/BSA alone (NOISE) or 50 ul of PBS/BSA containing the diluted conjugate (SIGNAL).

50 ul of one of the following reagents was added to each tube: distilled water, 1-propanol, 2-propanol, or ethanol. The final concentration of the alcohols in the tubes was 50% by volume.

To each tube was added 100 ul of 0.1N HCl. Immediately after addition of the 0.2N HCl, 300 ul of 0.2N NaOH containing 0.1% $H_2O_2$ was added to each tube and the signal from each tube was measured in LB950 Luminometer in CPS. The results are listed below in Table 4.

TABLE 4

| Reagent | Signal | Noise | S/N Ratio | S/N Ratio Relative to Control |
|---|---|---|---|---|
| Water (control) | 65885 cps* | 650 cps | 101.4 | 1 |
| 1-Propanol | 144065 cps | 665 cps | 216.6 | 2.1 |
| 2-Propanol | 137695 cps | 520 cps | 264.8 | 2.6 |

TABLE 4-continued

| Reagent | Signal | Noise | S/N Ratio | S/N Ratio Relative to Control |
|---|---|---|---|---|
| Ethanol | 127825 cps | 470 cps | 271.9 | 2.7 |

*Photon count per second (CPS)
All values are means of duplicate samples.

What is claimed is:

1. A method for enhancing the chemiluminescent signal of an acridinium ester in a chemiluminescent reaction which comprises oxidizing the acridinium ester under alkaline pH conditions in the presence of about 10 to 90% of a water-miscible alcohol wherein the water-miscible alcohol contains one to three carbon atoms.

2. A method as recited in claim 1 wherein the water-miscible alcohol contains one hydroxyl group.

3. A method as recited in claim 2 wherein the water-miscible alcohol is an isopropanol.

4. A method as recited in claim 1 wherein the effective amount of the water-miscible alcohol in the chemiluminescent reaction mixture is at least 10% by volume.

5. A method as recited in claim 4 wherein the effective amount of the water-miscible alcohol in the chemiluminescent reaction mixture is at least 50% by volume.

6. A method for enhancing the chemiluminescent signal from an acridinium ester encapsulated within a liposome vesicle, in a chemiluminescent reaction which comprises:
   a) contacting the liposome vesicle with an aqueous solution comprising about 10 to 90% of a first water-miscible alcohol to release the acridinium ester from the liposome vesicle; and
   b) oxidizing the acridinium ester so released under alkaline pH conditions in the presence of about 10 to 90% of a second water-miscible alcohol wherein the first and second water-miscible alcohols each contain one to three carbon atoms.

7. A method as recited in claim 6 wherein the first water-miscible alcohol is the same as the second water-miscible alcohol.

8. A method recited in claim 6 wherein the first and second water-miscible alcohols each contain one hydroxyl group.

* * * * *